United States Patent
Delafosse et al.

(10) Patent No.: US 8,999,729 B2
(45) Date of Patent: Apr. 7, 2015

(54) DEVICE AND ANALYZING SYSTEM FOR CONDUCTING AGGLUTINATION ASSAYS

(75) Inventors: Isabelle Delafosse, Greng (CH); Fabrice Ummel, La Chaux-de-Fonds (CH); Antonio Yanez, Salavaux (CH)

(73) Assignee: Symbion Medical Systems Sarl, Avenches (CH)

( * ) Notice: Subject to any disclaimer, the term of this patent is extended or adjusted under 35 U.S.C. 154(b) by 873 days.

(21) Appl. No.: 13/165,134

(22) Filed: Jun. 21, 2011

(65) Prior Publication Data

US 2011/0250617 A1 Oct. 13, 2011

Related U.S. Application Data

(63) Continuation of application No. PCT/EP2008/068260, filed on Dec. 23, 2008.

(51) Int. Cl.
| | |
|---|---|
| *G01N 33/558* | (2006.01) |
| *G01N 33/537* | (2006.01) |
| *G01N 33/538* | (2006.01) |
| *B01L 3/00* | (2006.01) |
| *G01N 33/53* | (2006.01) |
| *B04B 5/04* | (2006.01) |
| *B01L 9/06* | (2006.01) |

(52) U.S. Cl.
CPC .......... *B01L 3/5085* (2013.01); *G01N 33/5304* (2013.01); *G01N 33/538* (2013.01); *G01N 33/5375* (2013.01); *B01L 3/5021* (2013.01); *B01L 9/06* (2013.01); *B01L 2300/069* (2013.01); *B01L 2300/18* (2013.01); *B01L 2400/0409* (2013.01); *B04B 5/0421* (2013.01); *Y10S 436/81* (2013.01)

(58) Field of Classification Search
None
See application file for complete search history.

(56) References Cited

U.S. PATENT DOCUMENTS

| | | | | |
|---|---|---|---|---|
| 660,746 | A | * 10/1900 | Bausch et al. | ............ 494/20 |
| 3,468,474 | A | 9/1969 | Shoblom et al. | |
| 3,953,172 | A | * 4/1976 | Shapiro et al. | ......... 436/500 |
| 4,092,113 | A | 5/1978 | Hardy | |
| 4,226,531 | A | 10/1980 | Tiffany et al. | |
| 4,244,694 | A | 1/1981 | Farina et al. | |

(Continued)

FOREIGN PATENT DOCUMENTS

| | | |
|---|---|---|
| EP | 1450159 A2 | 8/2004 |
| WO | 9921658 | 5/1999 |

OTHER PUBLICATIONS

International Search Report for PCT/EP2008/068260 dated Sep. 22, 2009.

*Primary Examiner* — Chris L Chin
(74) *Attorney, Agent, or Firm* — Pearne & Gordon LLP (57) ABSTRACT

A device for conducting an agglutination assay comprising several reaction vessels, each reaction vessel comprising an upper chamber having an opening for accepting reactants and/or a sample; and a lower chamber comprising an end in communication with the upper chamber for receiving fluids from the upper chamber, a closed end opposite to the end, and a matrix for separating agglutinates from non-agglutinates; wherein the device further comprises a rotating support able to rotate around an axis and holding pivotally the reaction vessels in a way to allow the reaction vessels to pivot about an axis essentially perpendicular to the rotation axis of the support when the latter is rotated, such that the fluids remain in the upper chamber when the support is not rotated, and can flow from the upper chamber to the lower chamber and into the matrix when the support is rotated.

17 Claims, 7 Drawing Sheets

(56) References Cited

U.S. PATENT DOCUMENTS

| | | | |
|---|---|---|---|
| 5,266,268 A | 11/1993 | Antocci et al. | |
| 5,449,621 A * | 9/1995 | Klein | 436/45 |
| 5,491,067 A * | 2/1996 | Setcavage et al. | 435/7.25 |
| 5,512,432 A * | 4/1996 | Lapierre et al. | 435/5 |
| 5,552,064 A | 9/1996 | Chachowski et al. | |
| 5,650,068 A | 7/1997 | Chachowski et al. | |
| 5,780,248 A * | 7/1998 | Milchanoski et al. | 435/7.25 |
| 5,863,802 A * | 1/1999 | Yves et al. | 436/518 |
| 5,869,347 A | 2/1999 | Josef et al. | |
| 6,114,179 A * | 9/2000 | Lapierre et al. | 436/518 |
| 6,187,583 B1 * | 2/2001 | Milchanoski et al. | 435/287.6 |
| 6,945,129 B2 * | 9/2005 | Escal | 73/864.24 |

* cited by examiner

DEVICE AND ANALYZING SYSTEM FOR CONDUCTING AGGLUTINATION ASSAYS

FIELD

The present invention concerns the field of agglutination assays such as that involved in immunohematology, and particularly to vessels useful for conducting agglutination assays and separating agglutinates.

BACKGROUND

Immunological agglutination reactions are used for identifying various kinds of blood types and for detecting various kinds of antibodies and antigens in blood samples and other aqueous solutions. In a conventional procedure, a sample of red blood cells is mixed with serum or plasma in test tubes or microplates, and the mixture may then be incubated and centrifuged. Various reactions either occur or do not occur depending on, for example, the blood type of the red blood cells or whether certain antibodies are present in the blood sample. Typically, these reactions manifest themselves as clumps of cells or particles with antigens or antibodies on their surfaces, referred to as agglutinates. Thus, the absence or presence of agglutinates indicates that no reaction or a reaction has occurred, respectively, with the size and amount of agglutinates being a quantitative indicator of the level or concentration in the sample, or an indicator of the reaction strength, affinity of the complex for which the blood sample was tested.

Recently, systems have been developed in which the agglutination reaction is carried out in one portion of a vessel, and separation of agglutinated red cells is accomplished in another portion of the same vessel using a matrix which separates agglutinated cells from other components in the reagent/sample mixture. One such system is disclosed and described in U.S. Pat. Nos. 5,650,068 and 5,552,064 and are manufactured and sold by Ortho-Clinical Diagnostics Inc., Raritan, N.J., under the trademark BIOVUE. Such reaction vessels, hereinafter called "index card", are in the form of several, usually six, columns formed in a transparent cassette with each column having an upper chamber and a lower chamber wherein the upper chamber is of a wider diameter than the lower chamber. The lower chamber contains a matrix for separating agglutinated cells from non-agglutinated cells. The diameter of the lower chamber is narrow enough such that when reagents and samples are added to the upper chamber, typically using a pipette, the reagents and samples remain in the upper chamber, and do not enter into the lower chamber, unless an additional force is applied.

In this method, gel or glass bead microparticles are contained within the lower chamber. A reagent is dispensed in a diluent in the lower chamber, and test red blood cells are placed in the reaction upper chamber. The reaction vessel is then centrifuged. The centrifuging accelerates the reaction, if any, between the reagent and the blood cells, and also urges any cells toward the bottom of the columns. The glass beads or gel in the lower chamber act as a filter, however, and resist or impede downward movement of the particles in the column. As a result, the nature and distribution of the particles in the lower chamber after centrifuging provides a visual indication of whether any agglutination reaction occurred in the upper chamber, and if so, of the strength of that reaction.

A disadvantage of the "index card" lies in the difficulty in automating the testing procedure described above. Conventional blood analysis systems include a multitude of stations or assemblies, each of which performs one or more functions, and typically a significant amount of operator supervision and labor is needed to operate the systems. For instance, the index card must be moved from a first station to a second station in order to perform the introduction of fluids into the reaction vessel and perform centrifugation. A complex and expensive equipment is then required as well as significant operator time, care and skill to insure that each station operates properly.

Document U.S. Pat. No. 4,226,531 discloses a disposable multi-cuvette rotor for use in an analytical photometer where each cuvette is divided into adjoining sample and reagent/measuring chambers by a wedge-shaped element and reactants are transferred by centrifugal force from one chamber to the other (see also U.S. Pat. No. 5,266,268).

Document U.S. Pat. No. 4,244,694 discloses a reactor/separator device for use in solid phase immunoassays and comprising a column which is open at both ends, a retaining and filtering means disposed in said column and which is permeable to aqueous solutions when subjected to a centrifugal force, a reaction and separation chamber disposed in said column above said filtering means and containing at least one matrix having immobilized therein an antigen or antibody component for the separation of at least one of said components of an antigen-antibody system.

Document EP1450159 discloses an apparatus for conducting an agglutination assay comprising a first section for receiving a fluid and a second section for receiving the fluid of the first section upon application of a centrifugal force. The first and sections are disposed fixedly and horizontally on a rotating support.

Document U.S. Pat. No. 5,869,347 discloses a method of detecting an analyte in a test liquid by agglutination in a reaction vessel which contains a single compact, porous matrix and which, following the action of gravitational forces, allows qualitative or semi-quantitative determination of the agglutination reaction.

Documents U.S. Pat. No. 4,092,113, WO99/21658 and U.S. Pat. No. 3,468,474 disclose a device for preparing a plasma sample comprising a tube (two concentric tubes which are releasably connected together in U.S. Pat. No. 4,092,113) that can be centrifuged to separate out plasma from the blood.

Here, in order to achieve desired analysis accuracies, the rotor must have precise and stable dimensional accuracies that are uniform between the several cuvettes of the rotor. However, these are hard to achieve since the manufacture of such multi-cuvette requires two parts to be made by injection molding and welded to one another. There is also an unacceptable tendency for reactant (reagent or sample) material to spontaneously move or "wick" along the region between the upper surface of the cuvette and the side wall of the cuvette, resulting in premature initiation of the coagulation reaction and thereby distorting the accuracy of the clot formation measurement.

SUMMARY

An object of the present disclosure is therefore to propose a new device and method which overcomes at least some limitations of the prior art. The present disclosure also concerns a device and analyzing system for conducting agglutination assays that allows performing a complete agglutination assay in a single station.

More particularly, the present disclosure concerns a device for conducting an agglutination assay comprising several reaction vessels, each reaction vessel comprising an upper chamber having an opening for accepting reactants and/or a sample; and a lower chamber comprising an end in communication with the upper chamber for receiving fluids from the upper chamber, a closed end opposite to the end, and a matrix for separating agglutinates from non-agglutinates; the device further comprising a rotating support able to rotate around an axis and holding pivotally the reaction vessels in a way to allow the reaction vessels to pivot about an axis essentially perpendicular to the rotation axis of the support when the latter is rotated, such that the fluids remain in the upper chamber when the support is not rotated, and can flow from the upper chamber to the lower chamber and into the matrix when the support is rotated In an embodiment, both the support and the reaction vessels can be made in one piece, and/or can be made by a plastic injection molding process.

In another embodiment, the upper chamber of the reaction vessel can be eccentric with the lower chamber.

In yet another embodiment, the rotating support can comprise a receptacle concentric with the axis, and the underneath face of the support and/or the surface of the receptacle can comprise one or several ribs.

In yet another embodiment, the receptacle can extend below and above the plane of the rotating support.

The present disclosure further concerns an analysis system for performing agglutination reaction and separation assays comprising said device, a drive shaft adapted to fixedly hold the device, a heating unit concentric with the support of the device; and means to optically detect cluster agglutinate and/or band or button formation within the lower chamber.

In an embodiment, the drive shaft can fixedly hold the device with the support having its rotation axis essentially parallel with the drive shaft rotation axis.

In another embodiment, the device can be held in the drive shaft by fitting the receptacle into a conformal recess in the drive shaft.

In yet another embodiment, the underneath face of the support and/or the surface of a receptacle of the support can comprise one or several ribs cooperating with one or several corresponding grooves on the surface of the recess, in order to maintain the device in the drive shaft during centrifugation.

In yet another embodiment, the heating unit can be annular-shaped and adapted to heat the fluids in the upper chamber when the support is not rotating.

The disclosure also pertains to a method for conducting an agglutination assay comprising:
providing the analysis station;
incubating the reagents and sample in the upper chambers of the vessels while the support is not rotating;
centrifuging the reagents and sample by rotating the support in order to force to the fluids from the upper chamber to the lower chamber to the separation matrix; and
performing readings and interpretation of positive or negative agglutination reactions.

In an embodiment, the support comprises a receptacle and the method can further comprise the steps of: adding reagents and a sample into the receptacle and mixing them together; and pipetting the mixed reagents and sample into the upper chamber of the different reaction vessels; said steps being performed prior to said incubating the reagents and sample.

In another embodiment, the device can be disposed after completion of said performing readings and interpretation.

The device is simple and easy to fabricate. Since the support and the reaction vessels are fabricated by a plastic injection molding process, stable dimensional accuracies between the reaction vessels and the support can be obtained easily. The device allows performing a complete agglutination assay in a single station corresponding to the analysis system.

BRIEF DESCRIPTION OF THE DRAWINGS

The invention will be better understood with the aid of the description of an embodiment given by way of example and illustrated by the figures, in which.

DETAILED DESCRIPTION THE PREFERRED EMBODIMENTS

Figure 1:
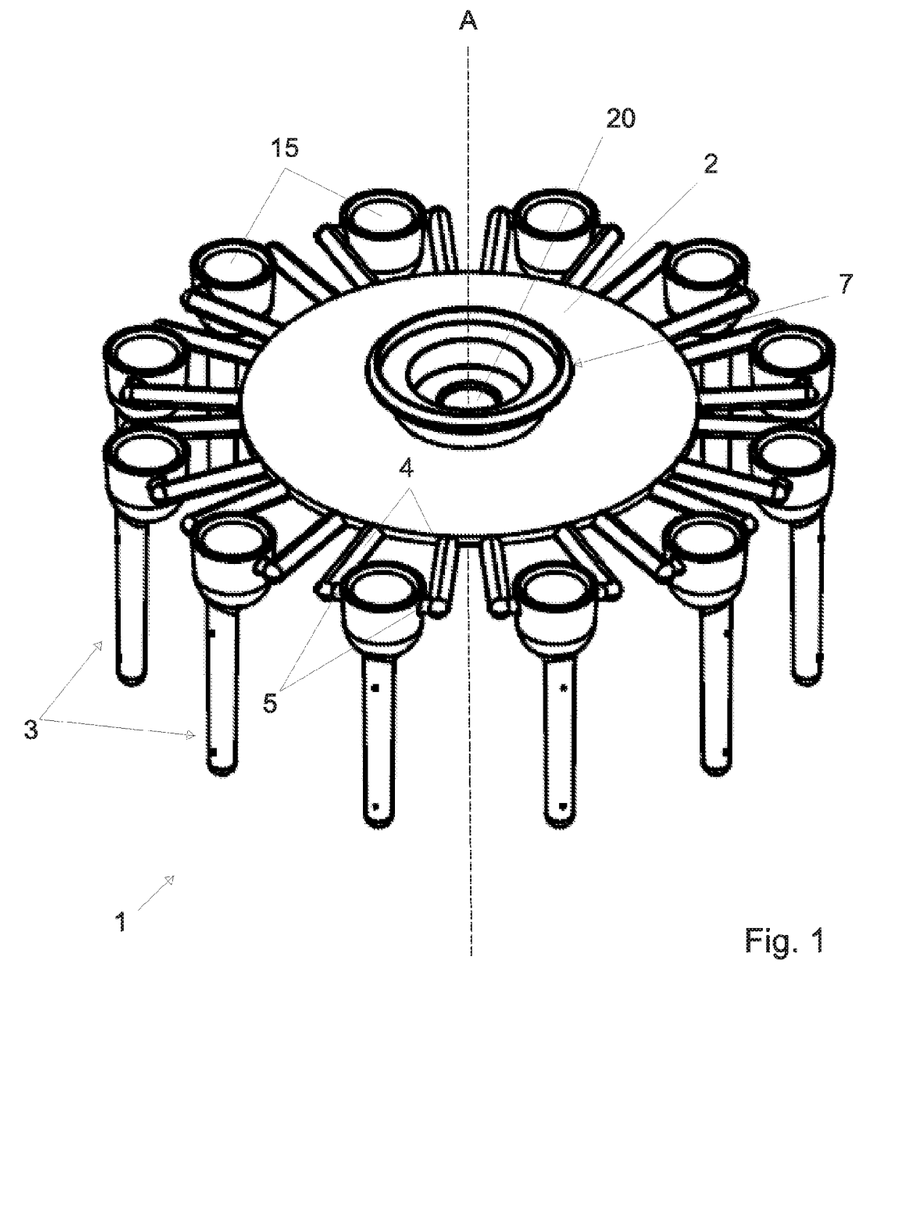
FIG. 1 shows a view of a device for conducting an agglutination assay and comprising several reaction vessels held in a support, according to an embodiment of the invention.
Figure 2:
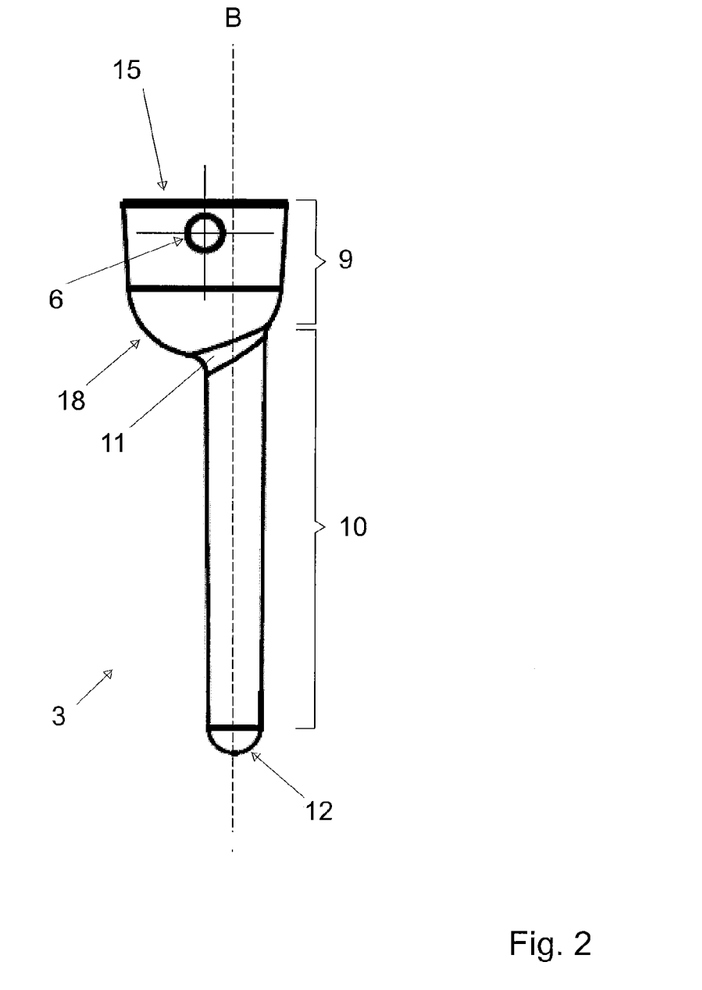
FIG. 2 shows a reaction vessel according to an embodiment of the invention.

The device 1 for conducting an agglutination assay according to an embodiment of the invention is shown in FIGS. 1 and 2. The device 1 comprises a support 2 having the form of a disc and comprising several reaction vessels 3 held along its periphery, pivotally around the support rotation axis A. The support 2 can comprise any practical number of reaction vessels 3, but typically six or more reaction vessels 3. In the preferred example of FIG. 1, twelve reaction vessels 3 are held equidistant along the support periphery. A large number of reaction vessels 3 allow for an increased number of simultaneous assays. Each reaction vessel 3 is pivotally held with a pair of holding arms 4, extending axially from the rotating support periphery. In the example of FIGS. 1 and 2, each arm comprises a pin 5 at its outer extremity, extending essentially perpendicular to the radial direction of the rotating support 2, the pin 5 being fitted into a corresponding hole 6 in the reaction vessel 3.

The reaction vessel 3 (FIG. 2) comprises an upper chamber 9 and a lower chamber 10, wherein the upper chamber 9 is of a wider diameter than the lower chamber 10, producing a shoulder area 18 between the upper and lower chamber 9, 10. The upper chamber 9 has an opening 15 for accepting fluid reactants and/or sample. The lower chamber 10 is typically an elongate tube, somewhat longer in proportion to its width, and aligned along a longitudinal axis B that is sensibly parallel with axis A when the support 2 is not rotated. The lower chamber 10 has a closed end 12, opposite to an open end 11 in communication with the upper chamber 9, permitting the fluids to flow from the upper chamber 9 to the lower chamber 10 when a force such as centrifugal force is applied. In the example of FIG. 2, the lower chamber 10 has essentially a cylindrical section, but other shapes are also possible. For example, the lower chamber 10 can have a conical section or have a first portion with conical section and another portion with a cylindrical section. Alternatively, the lower chamber 10 may have an elliptical section with substantially parallel sides.

The lower chamber 10 generally contains a matrix for separating agglutinates from non-agglutinates in the reaction mixture. Such a matrix may be comprised of any suitable material for separating agglutinates such as glass beads, polymer beads, filter paper, gel filtration media, sintered glass, plastics, such as described in patent EP0305337.

The wider upper chamber diameter facilitates the adding of the reagents and sample. The diameter of the lower chamber 10 is narrow enough such that when reagents and sample are added to the upper chamber 9, typically using a pipette, the fluids remain in the upper chamber 9, and do not enter into the lower chamber 10, preventing their passage through the matrix, unless an additional force (such as centrifugation) is applied to effect their movement. It is therefore possible to exert control over the timing of the agglutination assay.

In a preferred embodiment of the invention shown in FIG. 2, the upper chamber 9 is eccentric with the lower chamber 10. In this configuration, the reagents and sample can be pipetted in the shoulder area 18, also eccentric with the reaction vessel axis B, allowing the fluids to be retained in the upper chamber 9 for a certain period of time before they are introduced into the separation matrix of the lower chamber 10. This conformation reduces the risk of having fluids pipetted directly to the top of the separation matrix in the lower chamber 10 and not retained in the upper chamber 10 during the incubation phase.

Any other conformations of the support 2, able to hold the reaction vessels 3 pivotally about an axis essentially perpendicular to the support rotation axis A, are also possible. For example, in an embodiment not represented, the reaction vessels 3 are suspended by their shoulder area 18 in ball seats provided around the disc-shaped support periphery.

Figure 3:
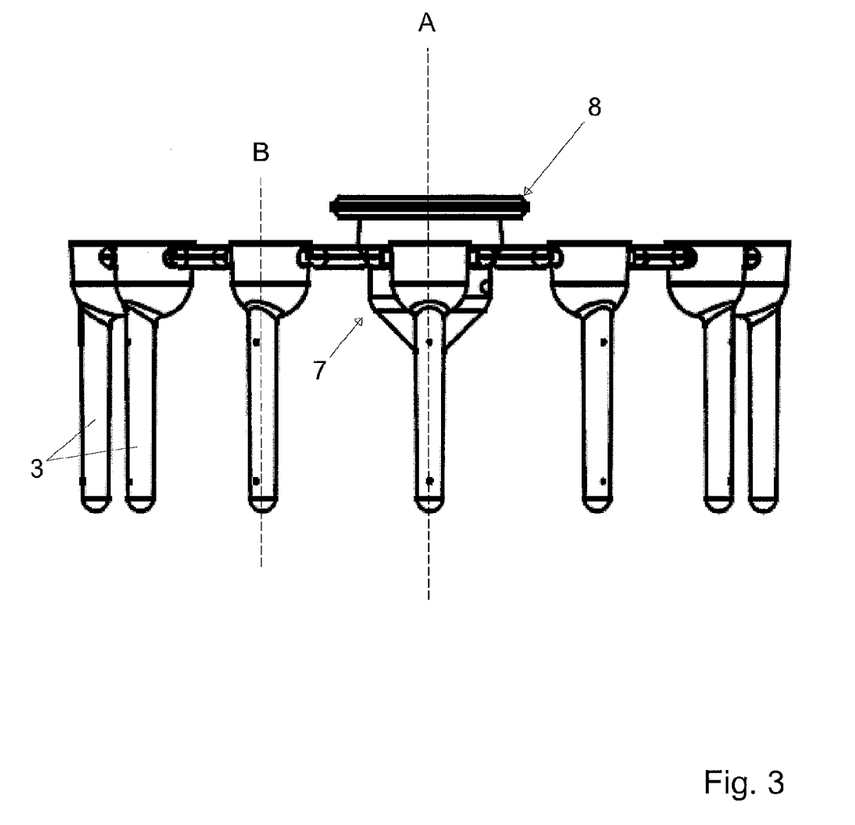
FIG. 3 represents the device viewed from the side and when not rotating.

As represented in FIG. 3, showing a lateral view of the device 1, the rotating support 2 comprises a cup-shaped receptacle 7 placed concentric with the rotation axis A. In the example of FIG. 3, the receptacle 7 extends below and above the plane of the rotating support 2, but could also be placed otherwise, such as completely below or above the plane of the rotating support 2. The receptacle 7 is destined to receive fluids preparations containing, for example, reactants, diluents and/or test sample such as red blood cells, plasma, etc.

In an embodiment of the invention, the device 1 also comprises a cover 8, able to close the receptacle 7, the cover 8 comprising an opening 20.

Figure 4:
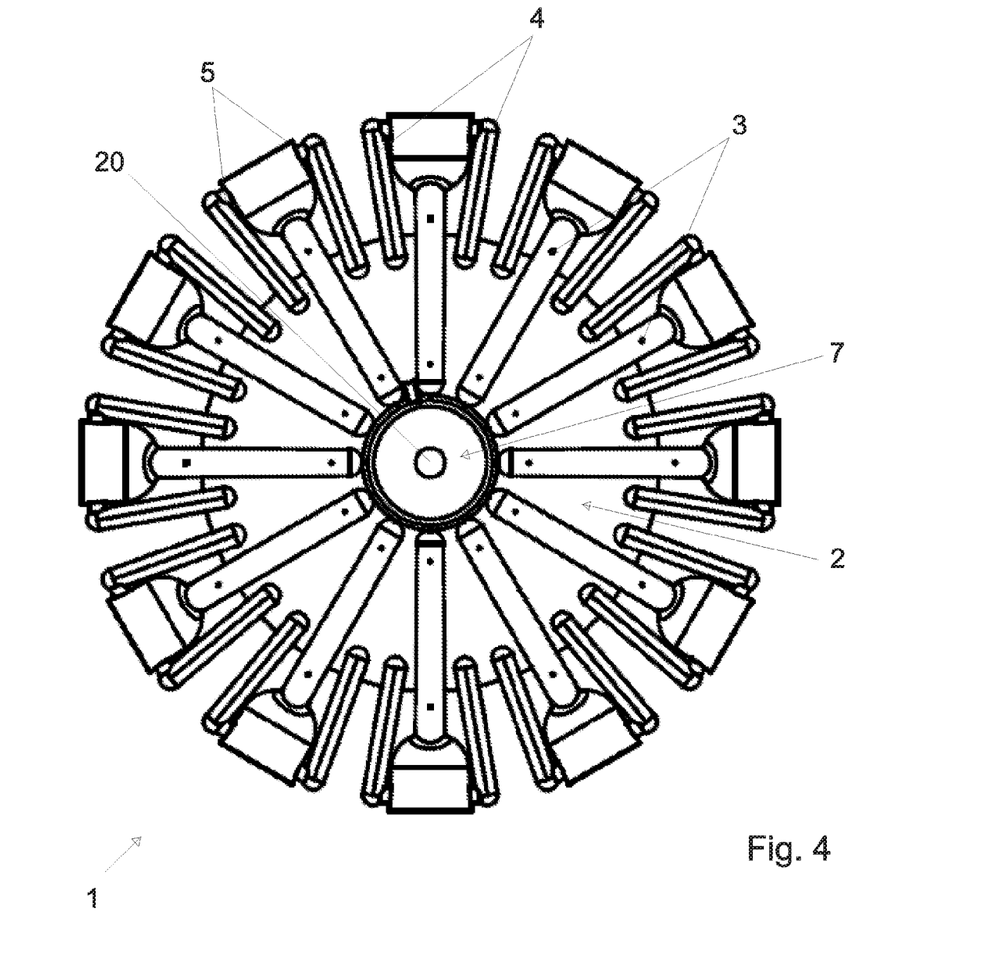
FIG. 4 illustrates the device of the invention where the reaction vessels are pivoted under the support.

FIG. 4 shows the device 1 of the invention where the reaction vessels 3 are pivoted under the support 2, the reaction vessels axis B being oriented essentially perpendicular with the support axis A, their closed ends 12 pointing towards the receptacle 7 and the support axis A. In this configuration, it is possible to form a stack of several devices 1 into one another, for example, in a storage unit prior to their use, resulting in significant savings on space and on packaging costs.

Figure 5:
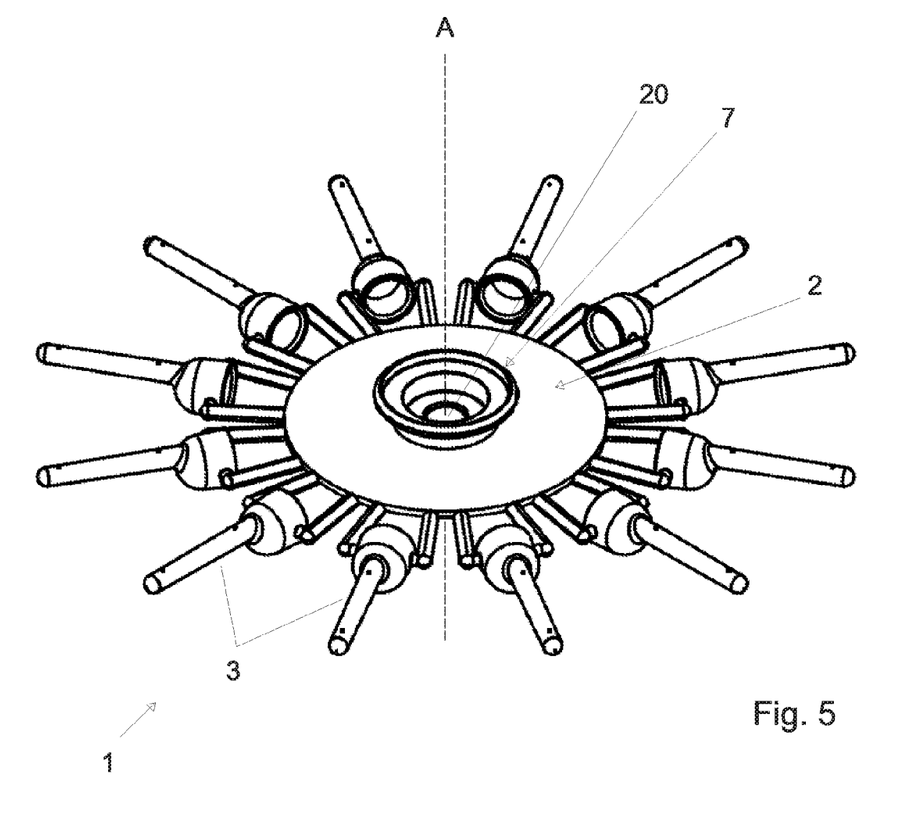
FIG. 5 shows the device during centrifugation.

FIG. 5 represents the device 1 when the support 2 is rotated, the reaction vessels 3 being pivoted in a way such as having their axis B essentially perpendicular with the support axis A, with their closed end 12 pointing opposite to the axis A.

In an embodiment of the invention, all parts of the device 1 are made from a single material. Such material can be any transparent material of suitable chemical resistance and absorption characteristics which will not interfere with the agglutination reaction or separation, and allowing for the visualization of the agglutinate reaction within the lower chamber 10. Examples of such materials include ultraviolet transmitting acrylics, polyolefins, styrenes, polycarbonates, combinations of butadiene and/or acrylonitrile with styrene, cellulosics, polyamides, and polyester resins.

In a preferred embodiment, the support 2, the cover 8 and the reaction vessels 3 are made from polypropylene, for example, by a plastic injection molding process. The support 2, the cover 8 and the reaction vessels 3 can be fabricated separately using three distinct plastic injection molds, respectively.

In another embodiment of the invention, the support 2 and the cover 8 are made in a single piece by the plastic injection molding process, using a unique mold.

Alternatively, the device 1 can be made from different materials. For example, the reaction vessels 3 can be made in one of the materials above and the other parts made in any other material. The lower chamber 10 may be substantially transparent in its entirety or only in selected areas as, for example, the area of agglutinate band formation in a positive sample.

Figure 6:
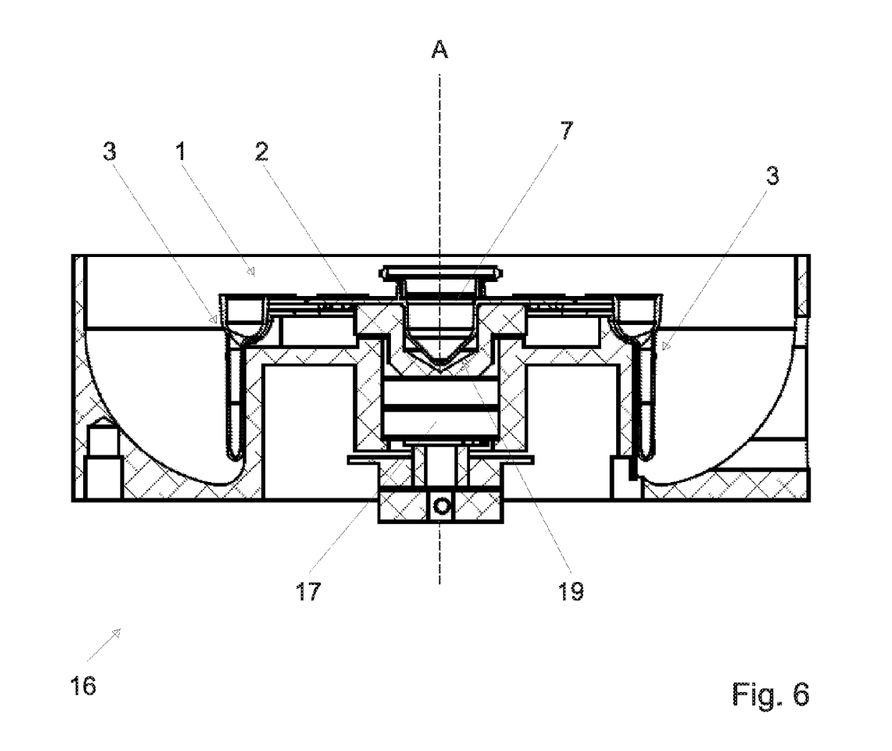
FIG. 6 represents an analysis system for performing an agglutination assay using the device 1 of the invention.
Figure 7:
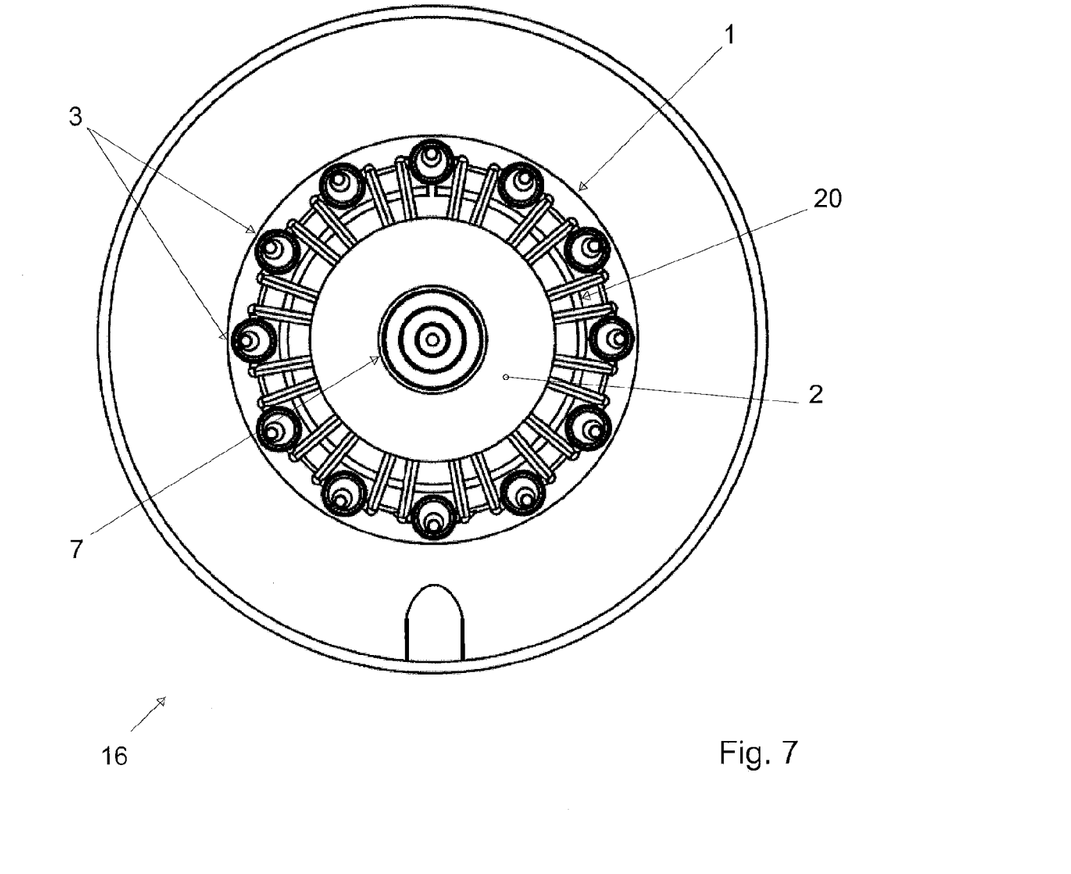
FIG. 7 is another view of the analysis system.

In a preferred embodiment, agglutination reaction and separation assays can be performed in a single analysis station when using the device 1 of the invention. An exemplary analysis station 16 for performing an agglutination assay using the device 1 is shown in FIGS. 6 and 7. The analysis station 16 comprises centrifugation means, here a drive shaft 17 driven by a motor (not shown) and able to fixedly hold the device 1 by, for example, fitting the receptacle 7 into a conformal recess 19 in the drive shaft 17. When fixed, the support 2 has its rotation axis A being essentially parallel and confounded with the drive shaft rotation axis.

The external surface of the receptacle 7 can comprise one or several ribs (not shown) cooperating with one or several corresponding grooves (also not shown) on the surface of the recess 19, in order to maintain the device 1 in the drive shaft 17 during centrifugation.

In an exemplary agglutination reaction and separation assay, the reagents and sample are added into the receptacle 7 through the opening 20 of the cover 8 and mixed together, for example, using the pipette or any other mixing means. The mixed reagents and sample are pipetted from the recipient 7 into the upper chamber 9 of the different reaction vessels 3, preferably into the shoulder area 18. Incubation is then performed when the support 2 is not rotating, the reaction vessels 3 being oriented with their axis B essentially parallel with the support axis A, as shown in FIGS. 1 and 3. The upper chamber 9 being eccentric with the lower chamber 10, the chance of any of the reagents being forced into the lower chamber 10 during sample addition is reduced. Moreover, the sample and reagents will tend to remain in the upper chamber during the incubation period. During the support 2 rotation, the fluids remaining in the receptacle 7 are retained by the cover 8.

As shown in the example of FIGS. 6 and 7, the analysis station 16 also comprises incubation means in the form of an annular-shaped heating unit (not shown) placed essentially concentric with the support 2, preferably disposed in proximity of the upper chamber 9, within the interior periphery formed by the reaction vessels 3. In this configuration, the heating unit is able to heat the fluids in the upper chamber 9 when the support 2 is not rotating. The heating unit typically comprises means to measure and control the temperature as know in the art. The heating unit can have any other configuration or position within the analysis system 16 as far as it is capable of heating the fluids in the upper chamber 9 when performing the incubation process.

After the incubation period, the support 2 is rotated by the drive shaft 17 at a rotation speed sufficient to apply a centrifugation force to the fluids in a direction substantially along the axis B, from the upper chamber 9 to the lower chamber 10, and to the separation matrix. During centrifugation, the reaction vessels 3 are pivoted with their axis B being essentially perpendicular with the support axis A, their closed end 12 pointing opposite to the axis A, as shown in FIG. 5.

As a result of the centrifugation, unagglutinated materials migrate down through the separation matrix while agglutinated cells remain on top of the separation matrix or are distributed within the matrix, depending on the degree of agglutination. Stronger agglutination reactions result in the cells remaining towards the upper portion of the separation matrix, while weaker agglutination reactions result in distribution of agglutinates at various distances from the top of the matrix.

The analysis system 16 can also comprise reading and interpretation means (not represented) for performing the observation of positive and negative agglutination reactions, the reading and interpretation means being designed to optically or otherwise detect cluster agglutinate and/or band or button formation within a certain area of the agglutination reaction zone in the lower chamber 10. Alternatively, observation can be performed manually.

After completion of an agglutination assay, such as the one described above, the device 1 can be disposed and a new assay can be performed with a new device 1. The device 1 can be easily handled.

In an embodiment of the invention, each device (1) is indexed. Here, for example, a device can be automatically picked from the stack described above, and put in the analysis system for performing a new agglutination assay. The whole assay can also be automated by performing the pipetting operations, incubation and centrifugation steps in an automatic fashion.

The device 1 of the invention allows performing a complete agglutination assay comprising the mixing, incubation and centrifugation steps in a single station corresponding to the analysis system 16 described above.

REFERENCE NUMBERS AND SYMBOLS

1 device
2 support
3 reaction vessel
4 arm
5 pin
6 hole
7 receptacle
8 cover
9 upper chamber
10 lower chamber
11 open end
12 closed end
15 opening
16 analysis station
17 drive shaft
18 shoulder area
19 recess
20 opening
A rotation axis of the support
B reaction vessel axis

The invention claimed is:

1. A device for conducting an agglutination assay comprising several reaction vessels, each reaction vessel comprising an upper chamber having an opening for accepting reactants and/or a sample; and a lower chamber comprising an end in communication with the upper chamber for receiving fluids from the upper chamber, a closed end opposite to the end, and a matrix for separating agglutinates from non-agglutinates; wherein
the device further comprises a rotating support able to rotate around an axis and holding pivotally the reaction vessels in a way to allow the reaction vessels to pivot about an axis essentially perpendicular to the rotation axis of the support when the latter is rotated, such that the fluids remain in the upper chamber when the support is not rotated, and can flow from the upper chamber to the lower chamber and into the matrix when the support is rotated.

2. The device according to claim 1, wherein the rotating support and/or the reaction vessels are made by a plastic injection molding process.

3. The device according to claim 1, wherein the rotating support is made of a single piece.

4. The device according to claim 1, wherein the rotating support comprises twelve reaction vessels.

5. The device according to claim 1, wherein the upper chamber is eccentric with the lower chamber.

6. The device according to claim 1, wherein the lower chamber is an elongate tube with a cylindrical section.

7. The device according to claim 1, wherein the rotating support comprises a receptacle concentric with the axis.

8. The device according to claim 7, wherein the underneath face of the support and/or the surface of the receptacle comprises one or several ribs.

9. The device according to claim 7, wherein the receptacle extends below and above the plane of the rotating support.

10. An analysis station for performing agglutination reaction and separation assays comprising:
a device containing several reaction vessels, each reaction vessel comprising an upper chamber having an opening for accepting reactants and/or a sample; a lower chamber comprising an end in communication with the upper chamber for receiving fluids from the upper chamber, a closed end opposite to the end, and a matrix for separating agglutinates from non-agglutinates; a rotating support able to rotate around an axis and holding pivotally the reaction vessels in a way to allow the reaction vessels to pivot about an axis essentially perpendicular to said rotation axis when the latter is rotated, such as to retain the fluids in the upper chamber when the support is not rotated and makes it flow from the upper chamber to the lower chamber and into the matrix when the support is rotated;
a drive shaft which fixedly holds the device at the rotating support;
a heating unit concentric with the support of the device; and
means to optically detect cluster agglutinate and/or band or button formation within the lower chamber.

11. The analysis station according to claim 10, wherein the drive shaft fixedly holds the device with the support having its rotation axis essentially parallel with the drive shaft rotation axis.

12. The analysis station according to claim 10, wherein the device is held in the drive shaft by fitting the receptacle into a conformal recess in the drive shaft.

13. The analysis station according to claim 10, wherein the underneath face of the support and/or the surface of a receptacle of the support comprises one or several ribs cooperating with one or several corresponding grooves on the surface of the recess, in order to maintain the device in the drive shaft during centrifugation.

14. The analysis station according to claim 10, wherein the heating unit is annular-shaped.

15. A method for conducting an agglutination assay comprising:
providing an analysis station comprising a device containing several reaction vessels, each reaction vessel comprising an upper chamber having an opening for accepting reactants and/or a sample; a lower chamber comprising an end in communication with the upper chamber for receiving fluids from the upper chamber, a closed end opposite to the end, and a matrix for separating agglutinates from non-agglutinates; a rotating support able to rotate around an axis and holding pivotally the reaction vessels in a way to allow the reaction vessels to pivot about an axis essentially perpendicular to said rotation axis when the latter is rotated, such as to retain the fluids in the upper chamber when the support is not rotated and makes it flow from the upper chamber to the lower chamber and into the matrix when the support is rotated; a drive shaft which fixedly holds the device at the rotating support; a heating unit concentric with the support of the device; and means to optically detect cluster agglutinate and/or band or button formation within the lower chamber;

incubating the reagents and sample in the upper chambers of the vessels while the support is not rotating;

centrifuging the reagents and sample by rotating the support in order to force to the fluids from the upper chamber to the lower chamber to the separation matrix; and performing readings and interpretation of positive or negative agglutination reactions.

16. The method according to claim 15, wherein the support comprises a receptacle and further comprising the steps of:

adding reagents and a sample into the receptacle and mixing them together; and pipetting the mixed reagents and sample into the upper chamber of the different reaction vessels;

said steps being performed prior to said incubating the reagents and sample.

17. The method according to claim 15, wherein the device is disposed after completion of said performing readings and interpretation.

\* \* \* \* \*